United States Patent [19]

Wahl et al.

[11] 4,302,204

[45] Nov. 24, 1981

[54] TRANSFER AND DETECTION OF NUCLEIC ACIDS

[75] Inventors: Geoffrey M. Wahl, Menlo Park; George R. Stark, Ladera, both of Calif.

[73] Assignee: The Board of Trustees of Leland Stanford Junior University, Stanford, Calif.

[21] Appl. No.: 54,200

[22] Filed: Jul. 2, 1979

[51] Int. Cl.$^3$ .................... C12Q 1/68; G01N 31/22; G01N 33/16; G01N 33/48

[52] U.S. Cl. ................... 23/230.3; 23/230 B; 422/56; 424/1.5; 435/6; 435/172; 435/805

[58] Field of Search ............ 435/6, 7, 172, 805; 23/230 B, 230.3, 230.6; 424/1, 2, 1.5; 422/56

[56] References Cited

U.S. PATENT DOCUMENTS 3,730,844  5/1973  Gilham et al. .................... 435/6
4,072,574  2/1978  Loeb et al. ....................... 435/6
4,139,346  2/1979  Rabbani .......................... 422/56

OTHER PUBLICATIONS

Wetmur, "Acceleration of DNA Renaturation Rates", *Biopolymers*, vol. 14, (1975), pp. 2517–2524.

Noyes et al., "Nucleic Acid Hybridization Using DNA Covalently Coupled to Cellulose", *Cell*, vol. 5, (1975), pp. 301–310.

Noyes et al., "Nucleic Acid Hybridization Using DNA Covalently Coupled to Cellulose", *Chem. Absts.*, vol. 83, No. 9, p. 247 (1975), Abs No. 160314x.

Wetmur, "Acceleration of DNA Renaturation Rates", *Chem. Absts.*, vol. 84, No. 7, p. 140 (1976), Abs. No. 39846g.

Reiser et al., "Transfer of Small DNA Fragments From Polyacrylamide Gels to Diazobenzyloxymethyl–Paper and Detection by Hybridization With DNA Probes", *Biochem. Biophys. Res. Comm.*, vol. 85, No. 3 (1978), pp. 1104–1112.

Kohne et al., "Room Temperature Method for Increasing the Rate of DNA-Association by Many Thousand Fold: The Phenol Emulsion–Association Technique", *Biochem.*, vol. 16, No. 24 (1977), pp. 5329–5341.

*Primary Examiner*—Thomas G. Wiseman
*Attorney, Agent, or Firm*—Bertram I. Rowland

[57] ABSTRACT

Improvements in the transfer and detection of separated nucleic acids, both RNA and DNA, are provided. For analysis of large DNA, the molecular weight segregated fractions of DNA are depurinated and fragmented to provide fractions having less than about 2 kb as single strands. With both RNA and DNA, the nucleic acid fractions are transferred after resolution to a chemically treated substrate and covalently affixed to the substrate. The resulting nucleotides affixed to the substrate are hybridized with labeled nucleotide probes and a volume exclusion agent, particularly a water soluble ionic polymer.

12 Claims, No Drawings

TRANSFER AND DETECTION OF NUCLEIC ACIDS

BACKGROUND OF THE INVENTION

1. Field of the Invention

The ability to probe the chromosome, extra chromosomal genetic material, messenger, transfer and ribosomal RNA, to synthesize genetic material, as well as to manipulate genetic material, has increased the need for means to analyze the composition and base order of genetic material. It is therefore desirable to provide for recording various genetic fragments which allow for hybridization with the complementary fragment, so that mixtures may be analyzed for the presence or absence of a particular nucleotide sequence. In the development of a system for analyzing for particular nucleotide sequences, there are many considerations. The first consideration is the ability to separate a mixture into its constituent parts, based on molecular weight and/or electrophoretic mobility. The second consideration is the ability to accurately determine the nature of the constituent parts.

One method for determining whether a particular sequence exists is hybridization. That is, a particular nucleotide sequence is marked with a detectable label, conveniently a radioactive label, and is combined with the nucleotide sequence to be analyzed. If the two sequences hybridize so as to form a strong non-covalent interaction, it may then be reasonably assumed that the sequences are substantially identical. Various techniques for accurately determining whether hybridization has occurred and for qualitatively or quantitatively determining the amount of the nucleotide sequence have been developed. There is a continuing interest and need for improved and more accurate techniques for the rapid determination of the presence of a particular DNA sequence.

2. Brief Description of the Prior Art

Southern, J. Mol. Biol. 98, 503 (1975) teaches the transfer of DNA fragments from electrophoretically resolved DNA in agarose gels as single strands to strips of nitrocellulose. Noyes and Stark teach the transfer of DNA and resulting immobilization to diazobenzyloxymethylcellulose, Cell, 5, 301 (1975). Alwine et al, PNAS, USA 74, 5350 (1977) teaches the detection of specific RNA's in agarose gels by transfer to diazobenzyloxymethyl-paper and hybridization with DNA probes. Reiser et al, Biochem. Biophys. Res. Comm. 85, 1104 (1978) teaches the transfer of small DNA fragments from polyacrylamide gels to diazobenzyloxymethyl-paper and detection with DNA probes. Wetmur, Biopolymers, 14, 2517 (1975) teaches the use of dextran sulfate for renaturation of DNA. See also U.S. Pat. No. 4,139,346.

SUMMARY OF THE INVENTION

Methods for determining the presence of a particular nucleotide sequence are provided, whereby a nucleotide sequence is transferred from a separation zone, e.g. electrophoretic gel, to a chemically reactive substrate, e.g. a diazo substituted paper, to become affixed to said substrate. Where the nucleotide sequence is DNA, the DNA is normally treated sequentially with acid, followed by base to provide for depurination, cleavage and denaturation to single stranded fragments of moderate molecular weight, which can be efficiently transferred to the paper and affixed. The nucleotide sequence which has been affixed can be determined by hybridization with a nucleotide sequence of known composition, employing a detectable label bonded to the sequence of known composition, or the affixed label can be used to determine the presence of a complementary nucleotide sequence in a composition to be assayed.

The affixed nucleotide sequences are found to be stable for long periods of time and capable of repeated hybridization, so that the paper may be used in assaying a number of different compositions. Greatly enhanced efficiency in hybridization is achieved by including in the hybridization medium a sufficient amount of a volume exclusion agent, particularly an ionic water soluble polymer.

DESCRIPTION OF THE SPECIFIC EMBODIMENTS

The subject invention involves the preparation of resolved nucleotide sequences covalently affixed to a stable substrate, which are then used for hybridization with nucleotide sequences for determination of the presence of a complementary nucleotide sequence. In an initial phase, a particular nucleotide sequence is prepared for transfer from a source of the sequence to a chemically reactive substrate, e.g. diazo substituted paper, to affix the nucleotide sequence to the substrate, by covalent bonding of the chemically reactive functionality to the polynucleotide, to provide for storage stability. When the nucleotide sequence has been previously subjected to resolution, particularly a resolution based on molecular weight and electrophoretic mobility, the position of the nucleotide sequence on the paper will be related to its chemical composition and molecular weight. Once the nucleotide sequence is transferred from the resolving medium to the substrate, hereafter referred to as paper, and covalently affixed to the paper, the paper may now be used for probing compositions having unknown nucleotide sequences to determine the presence of a sequence complementary to the affixed nucleotide sequence. A hybridization buffer is employed including a volume exclusion or renaturing agent, which greatly enhances the rate and efficiency at which a complementary nucleotide strand hybridizes to the affixed strand.

Prior to hybridization, DNA is treated differently from RNA. Depending upon the molecular weight of the DNA, during electrophoresis, differing mixtures of materials are employed to enhance resolution. Where relatively low molecular weight DNA is involved, cross-linked polymers are employed to provide for a hard polymer, where the cross-links therein are susceptible to cleavage without adverse affects on the DNA. Where the DNA is of a size in excess of about 200 bases in length, the DNA is subject to successive treatments of depurination and degradation and denaturation, so as to provide for randomly formed single stranded smaller fragments.

The nucleotide sequences to be assayed by the paper may be labeled, particularly with a radioactive marker. After hybridization, the presence of the radioactively marked nucleotide sequences may be determined by autoradiography. In this manner, the pesence or absence of a particular sequence can be determined, as well as a quantitative evaluation of its amount. By employing fragments, the method is particularly sensitive, since a fragment having a complementary sequence to the affixed nucleotide sequence may have an unhybridized tail which can oligomerize with a plurality of labeled sequences, so as to multiply the number of labels for each nucleotide sequence which hybridizes with the affixed nucleotide sequence.

The subject method provides for the separation of small DNA fragments obtained from restriction enzyme digests on polyacrylamide-agarose composite gels and transferring the denatured DNA to diazo activated paper, and detecting the affixed DNA by hybridization with radioactively labeled DNA probes. This procedure is useful for high resolution mapping of plasmid and viral DNAs, for detecting cloned DNA sequences within mixtures of DNA fragments protected by nucleosomes during digestion of chromatin with nucleases, and for mapping of binding sites of non-histone proteins in DNA and chromatin.

In discussing the subject invention, the various steps which are involved will be described individually followed by generalizations which cover the overall method.

RESOLUTION

The nucleotide sequences which are to be assayed are treated differently, depending upon whether RNA or DNA is involved. For RNA, before resolution by electrophoretic purification and separation, the RNA samples are normally purified, precipitated with ethanol and dried. Since large amounts of ribosomal RNA compete with transfer of mRNA, it is frequently desirable to purify the composition by selecting poly A+ RNAs with poly-U Sepharose or oligo-dT cellulose before electrophoresis, thus removing ribosomal RNA.

In performing the electrophoresis, agarose gel is normally employed. Desirably, the secondary structure of the RNA is disrupted, either by pretreatment with glyoxal or by performing the electrophoresis in the presence of methylmercuric hydroxide.

The DNA is electrophoretically resolved with agarose gels, frequently having a small portion of acrylamide, usually not exeeding about 12%. Depending upon the size of the DNA to be resolved, the hardness of the gel may be enhanced by cross-linking of the acrylamide. In order to enhance the transfer of small DNA nucleotide sequences, for example fewer than 50 base pairs, the cross-linking agent should be capable of cleavage by a reagent which does not adversely affect the chemical structure of the DNA. For example, the linking group may have a glycol functionality, which is readily cleaved by periodic acid. The amount of acrylamide generally ranges from about 5 to 12% for resolving fragments in the range of about 2,000 to 10 base pairs.

After the nucleotide sequences have been resolved by electrophoresis, the gel is then prepared for transfer to the paper. Because of the short lived nature of the diazo group, the two processes are normally performed concomitantly.

GEL PREPARATION AND TRANSFER

The RNA gel is treated differently, depending upon its history. Where the RNA was pretreated with glyoxal, the gel is treated with aqueous base, generally from about 10 to 100 mM under mild conditions for a sufficient time to substantially remove all the glyoxal from the RNA; and to cleave the RNA for efficient transfer. Where the mecuric compound has been employed, the mecuric compound is removed by reaction with a sulphur compound, for example mercaptoethanol. In each case, the gel is then washed with an appropriate buffer, while with the mecuric compound, an additive is included to react with the excess mercapto compound, e.g. iodoacetic acid. The buffer employed provides a mildly acidic pH generally under 5, preferably from about 3 to 5, more preferably about 4.

For DNA, particularly in cases of small DNA fragments ($\sim$10–100 bases) the acrylamide is cross-linked, and the cross-links are cleaved to enhance the efficiency of transfer of the small DNA fragments. In preparing the gel for transfer, the gel is treated with the cleaving reagent under conditions which do not adversely affect the DNA fragments. In contrast, where large DNA fragments are involved, cross-linked acrylamide is not required, and the gel is treated with mild acid to provide for degradation of the large DNA to randomly sized smaller fragments. The DNA is then treated with a denaturing agent, conveniently mild base, generally from about 0.2 to 1 M hydroxide, preferably about 0.5 M, to cleave and provide single strands. After sufficient time to denature the DNA, the gel is neutralized to a mildly acid pH, not lower than about 3, preferably about 4, for transfer.

The diazo substituted paper is prepared in substantially the same manner as has been described in Alwine et al, supra. Conveniently, 1-[(m-nitrobenzyloxy)-methyl] pyridinium chloride (NBPC) is added to the paper, preferably Whatman 540 paper, in an aqueous medium and the paper subsequently dried. After washing with a nonpolar solvent, the paper is dried and the nitro groups reduced by a convenient reducing agent, e.g. dithionite. After washing to remove the reductant and any hydrogen sulfide, the paper may be stored until required for use.

When the paper is to be used, the amino groups are diazotized, employing nitrous acid under mild conditions, so as to stabilize the diazo groups. The concentration of diazo groups should be sufficient to affix at least 5 $\mu$gm of single stranded nucleic acid per cm$^2$ of surface area, preferably at least 10 $\mu$gm per cm$^2$ of surface area.

TRANSFER

The transfer from the gel to the paper is substantially the same for both RNA and single stranded DNA. The diazotized paper is placed on top of the gel under a light weight in an appropriate buffer and the composite structure allowed to stand for a sufficient time under mild conditions (0° to 25° C.) to allow for the efficient transfer of the nucleotide sequences to the paper. The diazo groups form covalent bonds with the nucleic acid, particularly guanosine and uridine bases, and any unreacted diazo groups decompose to phenolic groups, which do not adversely affect the nucleic acids bound to the paper.

DETECTION OF NUCLEOTIDES

The paper to which the nucleic acids have been affixed can now be used in a number of ways. First, the nucleic acid composition affixed to the paper can be assayed by employing probes for known composition and hybridizing the nucleic acids bound to the paper with labeled, conveniently radioactively labeled, nucleic acids of known composition. Alternatively, where the nucleic acids bound to the paper are known, a nucleic acid of unknown composition could be probed by labeling the unknown composition with a marker, conveniently a radioactive marker, e.g. $^{32}$P, and after hybridizing, determining whether hybridization has occurred by autoradiography. (Labeling with $^{32}$P by nicktranslation with DNA polymerase 1 is described in Rigby et al, J.Mol.Biol. 113, 237 (1977)). Normally, the labeled ssDNA will be a mixture of complementary ssDNA capable of annealing and renaturation to dsDNA. The fragments are usually randomly sheared by a DNase, U.V. light, mechanical shearing or the like to provide the oligomers for hybridization.

Hybridization is carried out from an appropriate hybridization buffer solution. The aqueous solution will have from about 40 to 60, usually about 50 volume percent of another polar solvent, usually a low molecular weight organic solvent ($<100$ m.w.) e.g. formamide. In addition, there will be a number of additives for a variety of purposes to enhance the hybridization. Usually there will be from about 0.1 to 1.5 M saline and about 0.1 to 1.5 mM citrate; about 0.005 to 0.05 wt %/vol each of albumin, particularly serum albumin, a high molecular weight inert polysaccharide and a polar polymer e.g. polyvinylpyrrolidone, about 0.5 to 5 mg/ml of sonicated denatured DNA e.g. calf thymus or salmon sperm; and optionally from about 0.5 to 2% wt/vol glycine.

Also included in the medium is a sufficient amount of a volume exclusion additive as an annealing accelerating agent. The additive may achieve the result by antichaotropic effects, that is, ordering of the solvent, desolvating the medium with a strong solvent shell or other effects which are not known. As the additive, a polar water swellable or soluble polymer, particularly a charged saccharidic polymer, more particularly anionic saccharidic polymer, e.g., dextran sulfate, is employed. The polymer will generally be at least of about 10,000 molecular weight and not more than about 2 million molecular weight, usually being from about 100,000 to 1 million molecular weight, and preferably about 400,000 to 600,000 molecular weight. The amount of the additive will generally be at least about 2 weight percent of the hybridization buffer, more usually at least about 5 weight percent, and generally not more than about 25 weight percent, preferably about 8 to 15 weight percent, more usually about 10 percent.

In cleaving the DNA, it is desirable that for DNA of greater than about 2 kb, usually 1 kb, the DNA is treated with mineral acid. e.g. HCl, of from about 0.2 to 0.5 M, particularly about 0.2 to 0.3 M, to provide DNA fragments under about 2 kb, usually approximately 0.5-2 kb.

By employing the cleavage as described previously in combination with the annealing accelerating agent, efficient transfer of DNA to the paper is achieved so that enhanced signals can be obtained. In addition, because labeled fragments are used during hybridization, the labeled fragments are oligomerized, so as to have a plurality of labels e.g. radioactive atoms, for each hybridization event. With radioactive labels, this permits more rapid autoradiography with less background, so as to provide for sharply defined bands in the autoradiograph.

The following examples are offered by way of illustration and not by way of limitation.

EXAMPLES (All temperatures not otherwise indicated are centigrade. All parts and percents not otherwise indicated are by weight, except for mixtures of liquids, which are by volume.)

The following abbreviations are employed: DBM, diazobenzyloxymethyl; kb, kilobases; PALA, N-(phosphonacetyl)-L-aspartate; CAD, a multifunctional protein which comprises carbamyl-P synthetase, aspartate transcarbamylase, and dihydroorotase, the first 3 enzymes of UMP biosynthesis; SSC: 0.15 M NaCl and 0.015 M trisodium citrate; Denhardt's reagent: 0.2% (w/v) each of bovine serum albumin, polyvinyl pyrrolidone, and ficoll (MW 400,000); SDS, sodium dodecyl sulfonate.

EXAMPLE I

Preparation of NBM-paper

Cut a sheet of Whatman 540 paper to fit into the bottom of a rectangular enamel, stainless steel, or glass pan. The size of the paper can be much larger than the size of each gel. Float the pan on a water bath at about 60°. For each $cm^2$ of paper, prepare a solution of 2.3 mg of 1-[(m-nitrobenzoyloxy)methyl] pyridinium chloride (NBPC) (8.14 $\mu$moles, M.W. 280.7) and 0.7 mg of sodium acetate trihydrate in 28.5 $\mu$l of water. Pour the solution over the paper evenly, and using rubber gloves, push out any bubbles. Rub the solution evenly over the paper with a gloved hand, continuing until the paper is nominally dry. Dry one or more such papers further at 60° in an oven for about 10 min, remove them, adjust the temperature of the oven to 130° to 135°, place them back in the oven and bake them at this temperature for 30 to 40 min. Several sheets may be baked at one time, with as many as 3 overlapping. Wash the papers several times with water for a total of about 20 min and three times with acetone for a total of about 20 min, then dry them in the air. NBM-paper (nitrobenzyloxymethyl-paper) is the most stable form and will keep for many months in the refrigerator. It is simple to activate it before each use. Alternatively, the less stable amino form (ABM-paper) can be stored for 4° in a vacuum for as long as a year.

EXAMPLE II

Preparation of DBM-paper
(diazobenzyloxymethyl-paper)

To reduce NBM-paper, incubate it in a hood (to eliminate $SO_2$) for 30 min at 60° with 0.4 ml/$cm^2$ of a 20% (w/v) solution of sodium dithionite in water, with occasional shaking. Wash the resulting ABM-paper several times with large amounts of water for a few minutes, once with 30% acetic acid, then again with several changes of water. Be sure no odor of $H_2 S$ remains. Transfer the wet paper directly to 0.3 ml/$cm^2$ of ice-cold 1.2 M HCl. For each 100 ml of HCl, add with mixing, 2.7 ml of a solution of $NaNO_2$ in water (20 mg/ml), prepared immediately before use. Keep the paper in this solution on ice for 30 min or a little longer, with occasional swirling. After 30 min, a drop of the solution should still give a positive (black) reaction for nitrous acid with starch-iodide paper. Leave the paper in the ice-cold acid until preparation of the gel has been completed. Then pour off the acid, wash the paper rapidly twice with ice-cold water and twice with ice-cold transfer buffer (see below). Begin the transfer without delay—see below for timings relative to preparation of the gels.

EXAMPLE III

Preparation and electrophoresis of the RNA

Before electrophoresis, the RNA samples should be purified, precipitated with ethanol, and dried. Large amounts of ribosomal RNA compete with transfer of mRNAs from overlapping regions of the gel. Hence, it may be advisable to reduce this competition and to increase the concentration of a specific mRNA by selecting poly A+ RNAs with poly-U Sepharose or oligo-dT cellulose before electrophoresis. With two selections of oligo-dT cellulose, very little of the isolated RNA is ribosomal. The presence of rRNA reduces the signal in the positions of the mRNAs.

In order to disrupt secondary structure in the RNA completely, electrophoresis should be carried out in the presence of methylmercuric hydroxide, or after pretreatment of the RNA with glyoxal. In either case, the distance a particular RNA migrates is directly proportional to the logarithm of its molecular weight.

A. RNA from agarose gels containing methylmercuric hydroxide

The quantities of reagents specified are appropriate for a 150 ml gel. Rock the gel gently for 20 to 40 min (depending on the thickness of the gel) at room temperature in 200 ml of 50 mM NaOH containing 5 mM 2-mercaptoethanol. Wash the gel twice for 10 min each with 200 ml of 200 mM potassium phosphate buffer, pH6.5, containing 7 mM iodoacetic acid at room temperature and then twice at room temperature for 5 min each with 200 mM sodium acetate buffer, pH4.0. Reduction of the NBM-paper should be started at the beginning of the NaOH wash; alternatively, diazotization of the ABM-paper should be started 0.5 hr later.

B. RNA pretreated with glyoxal from agarose gels

Place the gel in 200 ml of 50 mM NaOH with or without ethidium bromide (1 μg/ml) for 1 hr at room temperature. Neutralize the gel by washing it twice for 15 min each with 200 mM sodium acetate buffer, pH4.0, (the ethidium bromide staining can now be observed). Reduction of the NBM-paper should be started about 0.5 hr after the NaOH wash; alternatively, diazotization of the ABM-paper should be started at the beginning of the first buffer wash.

EXAMPLE IV

Transfer to DBM-paper

Saturate two or three sheets of Whatman 3 MM paper with the same buffer used for the final wash of the gels, then place them in contact with a source of additional buffer. Place the gel on top of the wet paper and place the fresh DBM-paper on top of the gel, using Saran ® wrap at the edges of the gel to prevent the DBM-paper from touching the wet 3 MM paper below. Add two or three layers of dry 3 MM paper, several layers of paper towels and a weight. Allow the buffer to blot through the gel and DBM-paper overnight, either at room temperature or at 4°.

EXAMPLE V

Pretreatment and hybridization

For RNA pretreatment and hybridization, the same procedure may be employed as for DNA, described in Example VIII, except that 0.1% SDS (sodium dodecyl sulfate) is included in the medium both during the pretreatment and hybridization.

EXAMPLE VI

Transfer of small DNA fragments from composite gels

A. Gel electrophoresis

Restriction fragments are separated on polyacrylamide-agarose slab gels (23×14×0.15 cm) using Tris-acetate buffer (40 mM Tris hydrochloride, pH7.8, 20 mM sodium acetate, 2 mM EDTA). The same buffer is used in the electrode reservoirs. To prepare the gels, mix 8 ml of 10× concentrated gel buffer, 59 ml of water and 560 mg of agarose (BioRad) and dissolve the agarose by boiling. To the solution cooled to 50°, and an appropriate volume of 30% acrylamide stock solution (27.78 g of acrylamide plus 2.22 g of N,N'-diallyltartardiamide (BioRad) per 100 ml) and 0.25 ml of 10% ammonium persulfate. Gels containing a single concentration of polyacrylamide between 5 and 12% are used to resolve fragments in the size range 2000 to 10 base pairs, increasing polyacryamide with decreasing sizes. DNA samples should be precipitated with ethanol before electrophoresis. The electrophoresis is carried out at room temperature at 15 to 20 mA.

B. Preparation of the gels and transfer

Place the gel into 20 ml of 2% periodic acid and rock it gently for 15 min at 37° to cleave the cross-links. Rinse the gel with water and put it into 250 ml of 0.5 M NaOH for 10 min at room temperature to denature the DNA. Rinse the gel with water and neutralize it in 250 ml of 0.5 M sodium phosphate buffer, pH5.5, for 10 min at room temperature, and then put it into 250 ml of ice-cold 50 mM sodium phosphate buffer, pH5.5, until the DBM-paper is ready (no longer than 15 min). Diazotiazation of ABM-paper should start at the same time as the treatment with periodic acid; alternatively, reduction of NBM-paper should start about 0.5 hr sooner. Do the transfer as described in the procedure for RNA, except use 50 mM sodium phosphate buffer, pH5.5, at 4°.

EXAMPLE VII

Transfer of larger DNA fragments from agarose gels

A. Gel electrophoresis

Restriction fragments are separated on 0.5% agarose slab gels containing ethidium bromide (0.5 μg/ml) in both the gel and the buffer reservoirs. Use the electrophoresis buffer described in the previous example. Add the ethidium bromide to the molten agarose just before pouring the gel. Perform the electrophoresis at room temperature until the bromcresol purple dye marker has migrated about 12 cm (8 to 12 hrs).

B. Preparation of gels and transfer of DNA to DBM-Paper

The following protocol is designed for a 150 ml (14.5×13.5×0.8 cm) agarose gel and should be changed accordingly for smaller volumes. It is advantageous to use bromcresol purple as the tracking dye during electrophoresis since it provides a convenient indicator for monitoring pH changes during the later washes. All the procedures are done at room temperature. Place the gel in an enamel pan and shake it gently with two 250 ml portions of 0.25 M HCL for 15 min each. Decant the acid, wash the gel briefly with distilled water, and shake the gel with two 250 ml portions of 0.5 M NaOH, 1.0 M NaCl for 15 min each. Decant the NaOH-NaCl solution and shake the gel with two 250 ml portions of 1 M sodium acetate buffer, pH4.0, for 30 min each. Wash the diazo-paper with ice-cold 20 mM sodium acetate buffer, pH4.0, just before transfer, and perform the transfer in 1 M sodium acetate buffer, pH4.0 as follows.

Place the gel on top of two sheets of Whatman 3 MM paper (approximately 20×30 cm each) saturated with 1 M sodium acetate buffer (pH4.0) (or 20x SSC for transfer to nitrocellulose). Place sheets of Saran ® wrap on the Whatman paper around the perimeter of the gel to prevent contact between the paper layers to be placed above the gel and the saturated paper beneath the gel. Position the DBM-paper (or nitrocellulose) on top of the gel. Regions where the gel and paper are in contact should be free of air bubbles which may interfere with the transfer. Place two sheets of dry Whatman 3 MM paper on top of the DBM-paper (or nitrocellulose), then a 3-inch layer of paper towels, and finally a light weight, to insure even contact between the different layers. Allow the transfer to occur for 2 hrs or longer. It is not necessary to add buffer to the saturated paper during transfer.

EXAMPLE VIII

Pretreatment, Hybridization, and Detection of Specific DNA Sequences Bound to DNA-paper ot DNA-Nitrocellulose The sporadic appearance of high backgrounds, a major problem in two-phase hybridizations, is minimized by the following procedure. It is very important to follow the procedure exactly. The protocol is designed for a 9×13.5 cm paper.

Place DNA-solid support in 10 ml of 50% formamide (reagent grade), 5×SSC, 5×Denhardt's reagent, 50 mM sodium phosphate buffer (pH6.5), 1% glycine and 250-500 μg/ml sonicated denatured salmon sperm DNA (Sigma) in a polyethylene bag. Incubate at 42° for at least 1 hr. Remove as much of this solution from the bag as possible, but do not blot the filter. (The easiest method is to draw a rod over the open bag to extrude the liquid.) Prepare 10 ml of a solution of 50% formamide, 5×SSC, 1×Denhardt's reagent, 20 mM sodium phosphate buffer (pH6.5) and 100 μg/ml sonicated, denatured salmon sperm DNA, and 10% sodium dextran sulfate 500 (Pharmacia). (The dextran sulfate is added most conveniently as a 50% (wt/vol) aqueous solution, which is slightly yellow and quite viscous.) Add 9 ml of the complete mixture to the bag, wetting the paper thoroughly. Heat the remaining 1 ml to 65° for a few minutes to reduce the viscosity, then add the probe. Mix vigorously in a voetex and add to the bag. Seal the bag close to the paper and avoid trapping large air bubbles. Mix the solution in the bag thoroughly to insure uniform distribution of probe. Incubate the bag at 42° for 4-16 hrs. depending on the source and amount of the DNA being analyzed and quantity of probe being used. This procedure may also be used for hybridization probes to RNA-paper. In thise case, 0.1% sodium dodecyl sulfate should be included in the prehybridization and hybridization solutions to inhibit ribonuclease. Sodium dodecyl sulfate is not advantageous in hybridizations to DNA-paper.

Wash the paper with three 250 ml portions of 2×SSC, 0.1% sodium dodecyl sulfate for 5 min each at room temperature, then with two 250 ml portions of 0.1×SSC, 0.1% sodium dodecyl sulfate at 50° for a total of 30 min. The background (detected with a monitor) should be very low. If the background is unacceptably high at this point, continue washing with this buffer for an additional 30 min. Expose the x-ray film to the paper at $-70°$, using a Dupont Lighting Plus intensifying screen.

EXAMPLE IX

Determination of DNA Fragment Lengths Following Partial Depurination and Strand Cleavage in Agarose Gels DNA samples were separated by electrophoresis through a 0.8% agarose gel until the bromcresol purple dye marker was 1 cm from the origin. The DNA samples in one-half of the gel were then depurinated partially and cleaved by sequential treatment with acid and alkali as described below. A sample of γ DNA from strain $J^-_{am}Z^-_{am}$Vir, digested with restriction endonuclease HindIII and run in the other half of the gel, was treated with alkali alone to provide single-stranded molecular weight markers. Both halves were equilibrated with 30 mM NAOH, 2 mM EDTA (8 changes for 15 min each), and electrophoresis was resumed with this solvent until the dye marker was approximately 6 cm from the origin (16 hr). Fragments were visualized with 254 nm light after equilibrating the gel with 0.2 M sodium phosphate (pH6.5) containing 1 μg/ml of ethidum bromide.

EXAMPLE X

Preparation of End-labeled γ DNA Fragments

Ten μg of γ DNA from $J^-_{am}Z^-_{am}$Vir were cleaved with HindIII in a buffer containing 20 mM Tris-HCl (pH7.4), 60 mM $CaCl_2$, 7 mM $MgCl_2$, 100 μg/ml bovine serum albumin (Bethesda Research Laboratories) and 2 mM dithiothreitol in a total volume of 60 μl. Reverse transcriptase from avian myeloblastosis virus was then used to catalyze addition of [α-$^{32}$P]dCTP and [α-$^{32}$P]dGTP to the staggered ends of the restriction fragments. The HindIII restriction digest was diluted with an equal volume of 20 mM Tris-HCl (pH7.4), 20 mM NaCl, 400 μM dATP, 400 μM dTTP, 50 μCi each of the $^{32}$P-labeled triphosphates (Amersham/Searle, 300 Ci/mmole), and 16 units of reverse transcriptase (Life Sciences, Inc., St. Petersburg, Fla.). The reaction mixture was incubated at 37° for 1.5 hrs and reaction was stopped by adding 0.1 volume of a solution 1% in Sarkosyl and 125 mM in EDTA, followed by heating to 70° for 5 min. Unincorporated nucleotides were removed by filtering the mixture through a column of Biogel P-60, equilibrated with 10 mM Tris-HCl (pH7.4), 1 mM EDTA.

EXAMPLE XI

Preparation of End-labeled ΦX174 Viral DNA

ΦX174 viral DNA (5 μg, was incubated at room temperature with 0.20 M HCl for 5 min, followed by 0.50 M NaOH for 30 min to yield fragments 100–1000 bases long. The fragments were collected by ethanol precipitation and dissolved in 200 μl of 10 mM Tris-HCl (pH8.7), 1 mM $MgCl_2$. The 5'-phosphoryl groups were removed by incubation for 3 hrs at 37° with calf intestine alkaline phosphatase. Proteins were removed by extraction with phenol and the DNA was collected by precipitation with ethanol. The 5'-termini of the fragments were labeled with [γ-$^{32}$P]ATP (3000 ci/mmole, Amersham/Searle) using T4 polynuceotide kinase (PL Biochemicals).

The efficiency of transfer was assessed employing restriction fragments obtained as described in Example X, i.e. $\gamma$ J$^-_{am}$Z$^-_{am}$Vir DNA with HindIII. Transfer was found to be complete in 2 hrs and fragments in the size range 0.56–22.7 kb are all transferred at the same high efficiency to either DBM paper or to nitrocellulose. It should be noted, that fragments smaller than about 1 kb can be transferred to DBM-paper, but not effectively to nitrocellulose.

In order to test the use of dextran sulfate, DNA from a PALA-resistant mutant with approximately 7 times with wild-type number of CAD genes was digested with EcoR1, fractionated on an agrose gel and transferred to DBM-paper. Identical DNA-paper strips were hybridized with the same quantity of nick-translated probe in the presence of different levels of dextran sulfate. The time for the hybridization was 16 hrs and $5\times10^6$ cpm of nick-translated probe ($1\times10^6$ cpm/ml, $5\times10^7$ cpm/$\mu$g) was employed. The washed filters were autoradiographed for 10 hrs.

Comparing the signals obtained in the presence of 10% sodium dextran sulfate and in its absence as a function of time of hybridization, reveals that the signal obtained after only 2 hrs in the presence of dextran sulfate is 3–4 times greater than the signal obtained after 72 hrs in its absence. While enhanced background is observed by the use of dextran sulfate, by employing 5$\times$Denhardt's reagent prior to hybridization with the probe, the background is reduced substantially.

Also studied were the effects of dextran sulfate on the rates of hybridization to DNA-paper of single-stranded and double-stranded probes. Labeled single-stranded $\Phi$X-174 viral DNA, average length approximately 250 bases and nick-translated double-stranded $\Phi$X-174 replicative form DNA were hybridized to $\Phi$X-174 DNA-paper in the presence and absence of 10% dextran sulfate. Three to four times more single-stranded probe binds the DNA-paper in 12 hrs in the presence of dextran sulfate than in its absence. With the double-stranded probe, the rate in the presence of dextran sulfate was at least 15 times the rate in its absence, although enhancement of the absolute rate was less than usually observed.

Dextran sulfate can also be employed with hybridization to immobilized RNA, as previously indicated. Dextran sulfate also increases rates of hybridization in in situ hybridizations used to locate specific gene sequences in polytene chromosomes and to detect recombinant mammalian viruses in plaques. Detection of recombinant molecules in the plaque-filter and colony-filter methods should also be facilitated by dextran sulfate. The hybridization employing dextran sulfate need not be limited to DBM-paper, but may also be used with nucleic acid bonded to any substrate.

It is evident from the above results that novel and useful techniques have been provided for rapid determination of nucleic acids by appropriately immobilizing nucleic acids on an appropriate vehicle, followed by hybridization with detectable probes. While hybridization has involved the use of radioactive labels, it is evident that other lables could also be employed, such as fluorescers, enzymes or the like. By employing polymeric materials in the hybridization medium, the rate of hybridization is greatly enhanced, so that determinations can be quickly and accurately made as to the presence or absence of particular nucleotide sequences.

The subject method also allows for a rapid and accurate analysis of large DNA molecules, greater than about 1 kb. By electrophoretic separation of a DNA mixture, which includes large DNA molecules, the DNA in zones of high molecular weight are fragmented and denatured to provide moderate to small DNA molecular weight fragments (10 to 2000 kb). These DNA molecules are then readily transferred to the reactive substrate for subsequent hybridization and analysis with labeled probes or may themselves be labeled and hybridized with DNA-substrate of known composition.

Although the foregoing invention has been described in some detail by way of illustration and example for purposes of clarity of understanding, it is obvious that certain changes and modifications may be practiced within the scope of the appended claims.

What is claimed is:

1. A process for the analysis of polynucleotides of at least ten bases which comprises:
   combining a solid substrate having polynucleotides covalently affixed thereto with a hybridization solution containing labeled polynucleotides suspected of being complementary to said affixed polynucleotides and a charged polysaccharide of at least 10,000 molecular weight present in at least about 2 weight %; and
   detecting the presence of labeled polynucleotides annealed to said affixed polynucleotides.

2. A method according to claim 1, wherein said charged polysaccharide is present in at least about 5 weight %.

3. A method according to claim 2, wherein said charged polysaccharide is dextran sulfate.

4. A method according to claim 1, wherein said polynucleotide is RNA.

5. A method according to claim 1, wherein said polynucleotide is DNA.

6. A method according to any of claims 4 and 5, wherein said charged polysaccharide is dextran sulfate and is present in at least about 5 weight %.

7. A method for analyzing double stranded DNA in a mixture having DNA molecules having chain lengths greater than 1 kb which comprises:
   distributing said DNA mixture according to molecular weight on a polysaccharide gel by means of gel electrophoresis;
   fragmenting and denaturing said DNA to provide single stranded DNA of less than about 2 kb;
   transferring at least a portion of said fragmented single stranded DNA to a chemically reactive solid substrate to covalently bond said transferred DNA to said substrate to provide DNA-substrate;
   combining said DNA-substrate with a hybridizing solution containing labeled single stranded DNA suspected of being complementary to the DNA of said DNA substrate; and
   determining the presence of labeled DNA bound to said DNA of said DNA-substrate by means of said label.

8. A method according to claim 7, wherein said chemically reactive solid substrate is diazosubstituted paper.

9. A method according to claim 7, wherein said fragmenting and denaturing involves contacting said DNA zone with acid and base respectively.

10. A method according to any of claims 7 to 9, wherein said hybridizing solution contains a charged polymeric volume exclusion agent.

11. A method according to claim 10, wherein said agent is dextran sulfate of at least about 10,000 molecular weight present in at least about 10 weight %.

12. A method for analyzing double stranded DNA of chain length greater than about 1 kb in a mixture of DNA which comprises:
   distributing said mixture in a gel according to molecular weight by means of gel electrophoresis;
   fragmenting and denaturing at least a portion of said DNA by treating with acid and base successively to provide ssDNA of chain lengths less than about 2 kb;
   transferring said ssDNA to diazo substituted paper to covalently bind said ssDNA to said paper to provide DNA-paper;
   hybridizing radioactively labeled single stranded DNA in a hybridizing solution with said DNA paper, whereby complementary labeled ssDNA binds to said DNA paper and wherein said hybridizing solution is an aqueous solution of from about 40 to 60 volume % of a low molecular weight polar organic solvent and from about 5 to 25 weight % of dextran sulfate of from about 10,000 to 1 M molecular weight.

* * * * *